(12) United States Patent
Mercier et al.

(10) Patent No.: US 6,613,945 B1
(45) Date of Patent: Sep. 2, 2003

(54) RESOLUTION METHOD FOR A RACEMIC MIXTURE OF ALDEHYDES

(75) Inventors: François Mercier, Versailles (FR); Stéphane Lelievre, Saint Cyr l'Ecole (FR); François Mathey, Paris (FR); Michel Spagnol, Lyons (FR)

(73) Assignee: Rhodia Chimie, Billancourt Cedex (FR)

( * ) Notice: Subject to any disclaimer, the term of this patent is extended or adjusted under 35 U.S.C. 154(b) by 0 days.

(21) Appl. No.: 09/831,044

(22) PCT Filed: Nov. 4, 1999

(86) PCT No.: PCT/FR99/02700

§ 371 (c)(1), (2), (4) Date: Aug. 7, 2001

(87) PCT Pub. No.: WO00/27778

PCT Pub. Date: May 18, 2000

(30) Foreign Application Priority Data

Nov. 6, 1998 (FR) .............................. 98 14022

(51) Int. Cl.$^7$ .............................. C07F 9/535
(52) U.S. Cl. ............................ 568/12; 568/13; 568/14; 549/5; 549/6; 548/113; 544/84
(58) Field of Search .................. 568/12, 13, 14; 549/5, 6, 7; 548/112, 113; 546/22, 23; 544/195, 157, 84

(56) References Cited

U.S. PATENT DOCUMENTS 6,288,279 B1 * 9/2001 Mathey et al. ................. 568/12
2002/0042540 A1 * 4/2002 Mathey et al. ................. 568/12

OTHER PUBLICATIONS

Fuchs G.: "Enantiomer fractionation of phosphine oxides by preparative subcritical fluid chromatography" Journal of Chromatography, vol. 623, No. 2, 1992, pp. 329–336, XP002105406, Amsterdam NL, the whole document.

Jean Jacques et al, "Enantiomers, Racemates, and Resolutions" 1991, Krieger Publishing Company, Malabar, Florida (US) XP002105403, p. 335–339.

CA:112:215841 abs of Journal of chromatographic Science by Macaudiere et al 27(10) pp 583–591 1989.*

CA:113: 41238 abs of New Journal of Chemistry by Tambute et al 13(8–9) pp 625–637 1989.*

CA:116:59926 abs of Chirality by Siret et al 3(5) pp 427–435 1991.*

CA:118:124636 abs of Journal of Chromatography by Fuchs et al 623 (2) pp329–336 1992.*

CA:122:214460 abs of Journal of Chromatography A by Bargmann–Leyder et al 666(1–2) pp 27–40 1994.*

* cited by examiner

*Primary Examiner*—Jean F. Vollano
(74) *Attorney, Agent, or Firm*—Burns, Doane, Swecker & Mathis, L.L.P.

(57) ABSTRACT

The invention concerns a resolution method for a racemic mixture of aldehyde of formula (I).

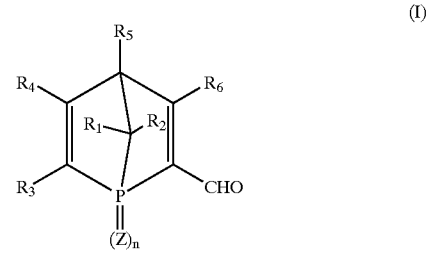

The aldehydes of formula I are useful in their enantiomeric form or their racemic form for preparing transition metal complexes useful as catalysts in hydroformylation reactions of olefins.

11 Claims, No Drawings

RESOLUTION METHOD FOR A RACEMIC MIXTURE OF ALDEHYDES

The application is a 371 of PCT FR/99/02700 filed Nov. 4, 1999, now WO 00/27778.

The present invention relates to a process for resolving a racemic mixture of aldehydes which can be used in their optically pure forms in the preparation of catalysts which may be used in olefin hydroformylation reactions.

A number of suitable catalysts which may be used in olefin hydroformylation are known in the art: these catalysts are complexes of a chiral phosphine with a transition metal such as rhodium or platinum. Of the chiral phosphines developed hitherto and acting as ligands for the rhodium or platinum, a distinction is made between the so-called class 1 phosphines in which the chiral centre is carried by the phosphorus (such as (2-methoxyphenyl)(methyl)(phenyl) phosphine), the so-called class 2 phosphines in which the chiral centre is carried by a carbon chain (such as (diphenyl) (2-isopropyl-5-methylphenyl)phosphine), and the class 3 phosphines carrying a chiral centre on the phosphorus and on a carbon chain, such as for example the following phosphine:

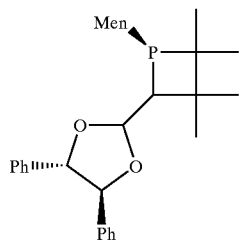

where Men denotes

The process according to the invention can be used in particular to resolve the aldehydes of formula A as follows, which carry at least two centres of asymmetry, the first on the phosphorus and the second on the carbon in position 4:

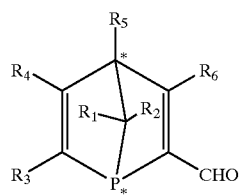

wherein $R_1$, $R_4$, $R_5$ and $R_6$, which may be identical or different, denote a hydrogen atom; a saturated or unsaturated, optionally substituted aliphatic hydrocarbon radical having 1 to 40 carbon atoms, wherein the hydrocarbon chain is optionally interrupted by a heteroatom; an optionally substituted carbocyclic or heterocyclic, saturated, unsaturated or aromatic, monocyclic or polycyclic radical; or a saturated or unsaturated aliphatic hydrocarbon radical wherein the hydrocarbon chain is optionally interrupted by a heteroatom and carries a carbocyclic or heterocyclic radical as hereinbefore defined, said radical optionally being substituted;

or $R_4$ and $R_5$ together with the carbon atoms which carry them form an optionally substituted saturated or unsaturated carbocyclic monocycle preferably having 5 to 7 carbon atoms;

$R_2$ denotes a hydrogen atom or the radical X;

$R_3$ denotes the radical X or the radical Y;

with the proviso that one and only one of the substituents $R_2$ and $R_3$ denotes the radical X;

X being selected from among a monocyclic or bicyclic aromatic carbocyclic or heterocyclic radical having 2 to 20 carbon atoms; a 1-alkenyl radical optionally having one or more additional unsaturated bonds in the hydrocarbon chain and having 2 to 12 carbon atoms; a 1-alkynyl radical optionally having one or more additional unsaturated bonds in the hydrocarbon chain and having 2 to 12 carbon atoms; a —CN; [$(C_1$–$C_{12})$ alkoxy]carbonyl; and [$(C_6$–$C_{18})$aryloxy]carbonyl radical;

Y having any of the meanings for $R_1$ with the exception of a hydrogen atom.

These phosphines belong to class 3.

More generally, the process of the invention can be used to resolve aldehydes of formula I:

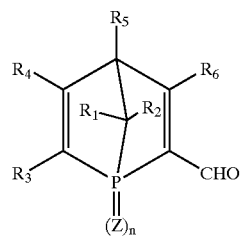

wherein $R_1$ to $R_6$ are as hereinbefore defined for formula A;

n denotes 0 or 1; and

Z denotes an oxygen or sulphur atom.

The aldehydes of formula A correspond to the compounds of formula I wherein n denotes 0.

The aldehydes of formula A have a rigid 1-phosphanorbornadiene structure which fixes the relative configuration of the two stereogenic centres consequently, these compounds are present in the form of a racemic mixture of only two stereoisomers (in spite of the presence of two asymmetric centres).

The aldehydes of formula I are more particularly useful, in their optically pure forms, as ligands of transition metals for preparing catalytic complexes in olefin hydroformylation reactions, hence the interest in a suitable resolution process.

After the failure of several attempts at resolution by chromatography on a chiral column, the inventors were led to perfect the resolution process according to the invention.

This process comprises the following steps:
a) reacting said compound of formula I with an optically active compound of formula II:

$$\begin{array}{c} A_1 \quad A_2 \quad A_3 \quad A_4 \\ \diagdown\!\diagup \quad \diagdown\!\diagup \\ HE \quad\quad GH \end{array} \quad\quad II$$

wherein
the group $>C(A_1)(A_2)$ is distinct from the group $>C(A_3)(A_4)$;

$A_1$, $A_2$, $A_3$, $A_4$ being independently selected from among a hydrogen atom; a ($C_1$–$C_{10}$)alkyl group; a ($C_6$–$C_{10}$)aryl group optionally mono- or polysubstituted by ($C_1$–$C_{10}$)alkyl, ($C_1$–$C_{10}$)alkoxy, amino, ($C_1$–$C_{10}$)alkylamino, di($C_1$–$C_{10}$)alkylamino or a halogen atom; a ($C_3$–$C_8$)cycloalkyl group optionally mono- or polysubstituted by ($C_1$–$C_{10}$)alkyl, ($C_1$–$C_{10}$)alkoxy, amino, ($C_1$–$C_{10}$)alkylamino, di($C_1$–$C_{10}$)alkylamino or a halogen atom; a saturated, unsaturated or aromatic 5- to 7-membered heterocyclic group having 1 to 3 heteroatoms selected from among O, N and S and optionally mono- or polysubstituted by ($C_1$–$C_{10}$)alkyl, ($C_1$–$C_{10}$)alkoxy, amino, ($C_1$–$C_{10}$)alkylamino, di($C_1$–$C_{10}$)alkylamino or a halogen atom; or $A_1$ and $A_3$ together form a ($C_2$–$C_6$)alkylene chain optionally mono- or polysubstituted by ($C_1$–$C_{10}$)alkyl, ($C_1$–$C_{10}$)alkoxy, amino, ($C_1$–$C_{10}$)alkylamino, di($C_1$–$C_{10}$)alkylamino or a halogen atom; or $A_1$ and $A_3$ together with the carbon atoms which carry them form a saturated 5- to 7-membered oxygenated heterocycle optionally comprising one to two additional heteroatoms selected from among O, N and S, said heterocycle optionally being mono- or polysubstituted by ($C_1$–$C_{10}$)alkyl, ($C_1$–$C_{10}$)alkoxy, amino, ($C_1$–$C_{10}$)alkylamino, di($C_1$–$C_{10}$)alkylamino, hydroxy or a halogen atom; and E and G:
either both denote an oxygen atom,
or independently denote a divalent —$NR_o$— radical wherein the $R_0$ groups independently denote a hydrogen atom, a ($C_1$–$C_{10}$)alkyl radical, a ($C_6$–$C_{10}$)aryl radical optionally substituted by ($C_1$–$C_{10}$)alkyl; or a ($C_6$–$C_{10}$)aryl-($C_1$–$C_{10}$)alkyl radical wherein the aryl moiety is optionally substituted by a ($C_1$–$C_{10}$) alkyl radical; so as to form a compound of formula III

III wherein $R_1$ to $R_6$, $A_1$ to $A_4$, E, G, Z and n are as hereinbefore defined, which is a mixture of diastereoisomers;

b) separating the diastereoisomers of formula III by a suitable method; and
c) regenerating the aldehyde function of each of the diastereoisomers of formula III, by hydrolysing the acetal function in an acid medium.

According to a first particularly preferred embodiment, the invention can be used to resolve compounds of formula I wherein:

$R_1$, $R_4$, $R_5$, $R_6$ independently denote a hydrogen atom or a T radical selected from among:
a saturated or unsaturated aliphatic hydrocarbon radical having 1 to 12 carbon atoms, wherein the hydrocarbon chain is optionally interrupted by a heteroatom selected from among O, N and S;
a monocyclic carbocyclic radical which is saturated or has 1 or 2 unsaturated bonds in the ring, having 3 to 8 carbon atoms;
a saturated or unsaturated bicyclic carbocyclic radical made up of 2 monocycles fused to each other, each monocycle optionally comprising 1 to 2 unsaturated bonds and having 3 to 8 carbon atoms;
an aromatic $C_6$–$C_{10}$ mono- or bicyclic carbocyclic radical.
a saturated, unsaturated or aromatic 5- to 6-membered heterocyclic monocyclic radical having 1 to 3 heteroatoms selected independently from among N, O and S;
a saturated, unsaturated or aromatic bicyclic heterocyclic radical made up of two 5- to 6-membered monocycles fused to each other, each monocycle having 1 to 3 heteroatoms selected independently from among O, N and S; and
a saturated or unsaturated aliphatic hydrocarbon radical, having 1 to 12 carbon atoms, wherein the hydrocarbon chain carries a monocyclic carbocyclic or heterocyclic radical as hereinbefore defined,
said radical T optionally being substituted;

$R_2$ and $R_3$ are as hereinbefore defined for formula I, with the proviso that:
Y may assume any of the meanings given hereinbefore for $R_1$ with the exception of a hydrogen atom; and
X is selected from among a ($C_2$–$C_6$) alkenyl group, a ($C_2$–$C_6$) alkynyl, phenyl, naphthyl, thienyl, furyl, pyrrolyl, imidazolyl, pyrazolyl, thiazolyl, pyridyl, pyrazinyl, pyridazinyl, isothiazolyl, isoxazolyl, benzofuryl, benzothienyl, indolyl, isoindolyl, indolizinyl, indazolyl, purinyl, quinolyl, isoquinolyl, benzothiazolyl and pteridinyl group; and
Z and n are as hereinbefore defined for formula I.

The nature of the substituent carried by T is very variable. Among the substituents used most, the following may be mentioned: ($C_1$–$C_6$)alkyl; ($C_2$–$C_6$)alkenyl; ($C_1$–$C_6$)alkoxy; ($C_2$–$C_6$)acyl; a radical selected from among: —$R_a$—OH, —$R_a$—$COOR_b$, —$R_a$—$NO_2$, —$R_a$—CN, —$R_a$—$N(R_b)_2$, —$R_a$—SH, —$R_a$—hal, —$R_a CF_3$ and —O—$CF_3$ (wherein $R_a$ denotes a bond or ($C_1$–$C_6$)alkylene, $R_b$, which may be identical or different, denote a hydrogen atom or ($C_1$–$C_6$) alkyl; and hal denotes halogen);
or the radical:

$$—R_c—\!\!\!\!\diagup\!\!\!\!\!\bigcirc\!\!\!\!\!(R_d)_m$$

where $R_d$ is selected from among ($C_1$–$C_6$)alkyl; ($C_2$–$C_6$)alkenyl; ($C_1$–$C_6$)alkoxy; ($C_2$–$C_6$)acyl; —$R_a$—

OH; —R$_a$—COOR$_b$; —R$_a$—NO$_2$; —R$_a$—CN; —R$_a$—N(R$_b$)$_2$; —R$_a$—SH; —R$_a$—hal; —R$_a$—CF$_3$ and —O—CF$_3$ (wherein R$_a$, R$_b$ and hal are as hereinbefore defined);

m denotes an integer between 0 and 5;

R$_c$ denotes a bond; (C$_1$–C$_6$)alkylene; —O—; —COO—; —NR$_b$—; —S—; —SO$_2$—; R$_b$ being as hereinbefore defined.

According to a second preferred embodiment, the compounds of formula I wherein:

R$_1$ and R$_4$ independently denote a hydrogen atom; a (C$_1$–C$_6$)alkyl group; a phenyl group optionally mono- or polysubstituted by (C$_1$–C$_6$)alkyl, (C$_1$–C$_6$)alkoxy, amino, (C$_1$–C$_6$)alkylamino, di(C$_1$–C$_6$)alkylamino or a halogen atom; a naphthyl group optionally mono- or polysubstituted by (C$_1$–C$_6$)alkyl, (C$_1$–C$_6$)alkoxy, amino, (C$_1$–C$_6$)alkylamino, di(C$_1$–C$_6$)alkylamino or a halogen atom;

R$_5$ denotes a hydrogen atom or a (C$_1$–C$_6$)alkyl group;

R$_6$ denotes a hydrogen atom; a (C$_1$–C$_6$)alkyl group; (C$_3$–C$_8$)cycloalkyl optionally mono- or polysubstituted by (C$_1$–C$_6$)alkyl, (C$_1$–C$_6$)alkoxy, amino, (C$_1$–C$_6$)alkylamino, di(C$_1$–C$_6$)alkylamino or a halogen atom; or phenyl optionally mono- or polysubstituted by (C$_1$–C$_6$)alkyl, (C$_1$–C$_6$)alkoxy, amino, (C$_1$–C$_6$)alkylamino, di(C$_1$–C$_6$)alkylamino or a halogen atom;

R$_2$ denotes a hydrogen atom or the radical X;

R$_3$ denotes the radical X or the radical Y;

with the proviso that one and only one of the substituents R$_2$ and R$_3$ denotes the radical X;

X denotes a C$_2$–C$_6$ alkenyl group; a C$_2$–C$_6$ alkynyl- group; or a phenyl radical; and Y has any of the meanings given hereinbefore for R$_1$ with the exception of a hydrogen atom;

n and Z being as hereinbefore defined for formula I, are resolved.

According to a third preferred embodiment, the compounds of formula I as hereinbefore defined for the second embodiment, where either R$_1$ and R$_2$ denote a hydrogen atom; R$_3$ denotes phenyl optionally mono- or polysubstituted by (C$_1$–C$_6$) alkyl; (C$_1$–C$_6$)alkoxy; amino; (C$_1$–C$_6$)alkylamino; di(C$_1$–C$_6$)alkylamino or a halogen atom or R$_1$ and R$_3$ independently denote phenyl optionally mono- or polysubstituted by (C$_1$–C$_6$)alkyl; (C$_1$–C$_6$) alkoxy; amino (C$_1$–C$_6$)alkylamino; di(C$_1$–C$_6$) alkylamino or a halogen atom; and R$_2$ denotes phenyl, are resolved.

More generally, when R$_1$, R$_4$, R$_5$, R$_6$ and Y comprise an aliphatic hydrocarbon radical interrupted by a heteroatom, the heteroatom is selected from among an oxygen atom, a nitrogen atom, a sulphur atom or a phosphorus atom, the oxygen and nitrogen atoms being preferred. When the atom which interrupts the chain is nitrogen, this is substituted by a hydrogen atom or a saturated or unsaturated C$_1$–C$_{10}$ hydrocarbon radical, preferably (C$_1$–C$_{10}$)alkyl. When the atom which interrupts the chain is phosphorus, this is substituted by (i) hydrogen or a C$_1$–C$_{10}$ hydrocarbon radical, preferably (C$_1$–C$_{10}$)alkyl, or by (ii) an oxo group.

By alkyl is meant a straight-chain or branched aliphatic hydrocarbon chain. Similarly, in the alkoxy, arylalkyl, alkylamino and dialkylamino radicals, the alkyl moieties denote straight-chain or branched hydrocarbon chains.

Examples of (C$_6$–C$_{18}$)aryl radicals include, in particular, phenyl, naphthyl, phenanthryl and anthryl.

The cycloalkyl radicals may be, for example, cyclopropyl, cyclobutyl, cyclopentyl, cyclohexyl, cycloheptyl and cyclooctanyl.

When A$_1$ and A$_3$ together with the carbon atoms which carry them form a 5- to 7-membered oxygenated heterocycle optionally comprising 1 to 2 additional heteroatoms, this is preferably the residue of a glucide such as α-D-glucose, for example.

When one of R$_1$, R$_4$, R$_5$, R$_6$, X or Y denotes a polycyclic (for example bicyclic) radical, this radical preferably comprises at least two rings fused to each other, i.e. two rings having at least two atoms in common. The polycyclic compounds are generally such that the number of carbon atoms in each ring varies from 3 to 7, preferably 5 to 6.

Examples of saturated monocyclic carbocyclic radicals might be the cyclopropane, cyclobutane, cyclopentane, cyclooctane and cycloheptane.

The preferred bicyclic carbocyclic radicals are the saturated derivatives of naphthalene and indene or those having one or more unsaturated bonds.

The preferred aromatic carbocyclic radical is benzene or naphthalene.

Preferred monocyclic heterocyclic radicals are the saturated or unsaturated derivatives of thiophene, furan, pyran, pyrrole, imidazole, pyrazole, thiazole, pyridine, pyrazine, pyrrolidine, pyridazine, morpholine, isoxazole and isothiazole.

Examples of heterocyclic bicyclic radicals are the saturated or unsaturated derivatives of benzofuran, benzothiophene, chromene, indole, indolizine, isoindole, indazole, purine, quinoline, phthalazine, naphthyridine, quinoxaline, quinazoline, cinnoline, isoquinoline, benzothiazole and pteridine.

By unsaturated derivatives are meant derivatives having one or more unsaturated bonds.

Examples of aromatic mono- or bicyclic heterocyclic radicals include, in particular:

furan, pyrrole, imidazole, pyrazole, thiazole, pyridine, pyrazine, pyridazine, isothiazole, benzofuran, benzothiophene, indole, isoindole, indolizine, indazole, purine, quinoline, isoquinoline, benzothiazole and pteridine.

The 1-alkenyl or 1-alkynyl radical may have one or more additional unsaturated bonds such as additional double or triple bonds. It is essential according to the invention that the carbon of said 1-alkenyl or 1-alkynyl radical which is directly linked to the 1-phosphanorbornadiene nucleus is an sp$_2$ or sp carbon.

These radicals have the following respective formulae:

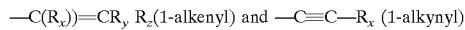

where R$_x$, R$_y$ and R$_z$ independently denote an alkyl group which is saturated or has one or more unsaturated bonds selected from among double or triple carbon-carbon bonds.

When R$_4$ and R$_5$, together with the carbon atoms which carry them, form a saturated or unsaturated carboxylic monocycle, this preferably has 6 carbon atoms.

When R$_1$, R$_4$, R$_5$, R$_6$ or Y denotes an aliphatic radical carrying a carbocyclic or heterocyclic monocyclic radical, this radical is preferably a (C$_6$–C$_{10}$)aryl-(C$_1$–C$_6$)alkyl such as a benzyl or (C$_3$–C$_8$)cycloalkyl-(C$_1$–C$_6$)alkyl group.

Particular values of the substituents R$_1$, R$_4$, R$_5$, R$_6$ and Y are as follows:

(i) R$_1$, R$_4$, R$_5$, R$_6$ and Y which may be identical or different denote a substituted phenyl radical of formula (a)

wherein p denotes an integer between 0 and 5;
Q$_3$ denotes(C$_1$–C$_6$)alkyl; (C$_2$–C$_6$)alkenyl; (C$_1$–C$_6$) alkoxy; (C$_2$–C$_6$)acyl; a radical selected from among: —R$_7$—OH, —R$_7$—COOR$_8$, —R$_7$—NO$_2$, —R$_7$—CN, —R$_7$—N(R$_8$)$_2$, —R$_7$—SH, —R$_7$—hal, —R$_7$—CF$_3$, —O—CF$_3$ (where R$_7$ denotes a bond or (C$_1$–C$_6$)alkylene; R$_8$, which may be identical or different, denotes a hydrogen atom or (C$_1$–C$_6$)alkyl; and hal denotes halogen);
or Q$_3$ denotes:

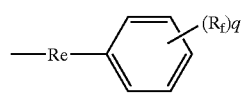

where R$_f$ is as hereinbefore defined for Q$_3$ with the exception of (b):
q denotes an integer between 0 and 5;
R$_e$ denotes a bond; (C$_1$–C$_6$)alkylene; —O—; —COO—; —NR$_8$—; —S—; —SO$_2$—; R$_8$ being as hereinbefore defined;
with the proviso that, when p is greater than 1, two Q$_3$ radicals attached to two successive carbon atoms of the phenyl nucleus may be linked together and form a bridge of formula —O—R$_8$—O— wherein R$_8$ denotes (C$_1$–C$_6$)alkylene;

(ii) R$_1$, R$_4$, R$_5$, R$_6$ and Y, which may be identical or different, denote a radical of formula:

wherein:
r is equal to 0, 1, 2 or 3
Q$_4$ denotes one of the following groups or functions:
  a hydrogen atom,
  a straight-chain or branched alkyl radical, having 1 to 4 carbon atoms,
  a straight-chain or branched alkoxy-radical having 1 to 4 carbon atoms,
  an —OH group,
  an NH$_2$ group,
  an NO$_2$ group,
  a phenyl radical,
  a halogen atom,
  a CF$_3$ group.
More preferably, the radicals Q$_4$ which may be identical or different are a hydrogen atom or a C$_1$–C$_4$ alkyl radical.

iii) R$_1$, R$_4$, R$_5$, R$_6$ and Y, which may be identical or different, are selected from among the phenyl, tolyl or xylyl, 1-methoxyphenyl and 2-nitrophenyl radicals and the biphenyl, 1,1'-methylenebiphenyl, 1,1'-isopropylidenebiphenyl, 1,1'-carboxybiphenyl, 1,1'-oxybiphenyl and 1,1'-iminobiphenyl radicals;

iv) R$_1$ and R$_5$, which may be identical or different, denote a hydrogen atom or a C$_1$–C$_6$ alkyl radical;

v) R$_4$ denotes a hydrogen atom; a (C$_1$–C$_6$)alkyl radical; phenyl optionally substituted by one, two or three substituents selected from among (C$_1$–C$_4$)alkyl and (C$_1$–C$_4$)alkoxy; or naphthyl;

vi) R$_6$ denotes (C$_1$–C$_6$)alkyl, (C$_3$–C$_8$)cycloalkyl or phenyl.

Preferred meanings of the radical X are an aromatic C$_6$–C$_{10}$ mono- or bicyclic carbocyclic radical; a 5- to 6-membered aromatic monocyclic heterocyclic radical having 1 or 2 heteroatoms selected independently from among N, O and S; a bicyclic aromatic heterocyclic radical made up of two 5- to 6-membered rings fused to each other, each ring having 1 or 2 heteroatoms selected independently from among O, N and S; a 1-alkenyl radical with 2 to 6 carbon atoms; a 1-alkenyl radical with 2 to 6 carbon atoms; —CN; [(C$_1$–C$_6$)alkoxy]carbonyl or [(C$_6$–C$_{18}$)aryloxy]carbonyl.

The preferred examples of carbocyclic and heterocyclic radicals are those mentioned hereinbefore within the scope of the definition of the substituents R$_1$, R$_4$, R$_5$ and R$_6$.

Preferably, X denotes a C$_2$–C$_6$ 1-alkenyl radical, a C$_2$–C$_6$ 1-alkenyl radical or a phenyl radical.

Compounds of formula I to which the resolution process according to the invention applies more particularly are:
  2-formyl-3,6-diphenyl-4,5-dimethyl-1-phosphanorborna-2,5-diene;
  2-formyl-3,6,7,7-tetraphenyl-1-phosphanorborna-2,5-diene.

The first step of the process of the invention (step a) consists in preparing an acetal or an aminal of the starting aldehyde of formula I by reacting this aldehyde, in the form of a racemic mixture, with a chiral 1,2-diol or an optically active 1,2-diamino derivative of formula II.

At the end of this step a pair of two diastereoisomers are obtained having different physico-chemical properties.

When the compound of formula II used in step a) corresponds to the formula:

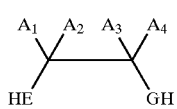

II wherein E and G both denote an oxygen atom, the compound of formula III obtained is an acetal of formula IIIa:

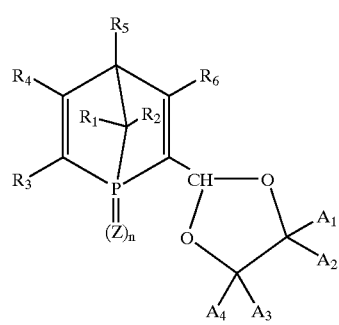

IIIa

When the compound of formula II corresponds to formula

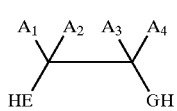

II wherein E and G independently denote a group NR$_o$, the compound of formula III obtained is an aminal of formula IIIb:

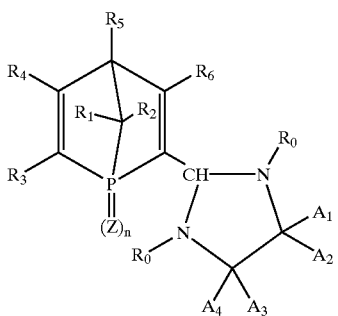

IIIb where the groups $R_0$ independently denote hydrogen, $(C_1-C_{10})$alkyl, optionally substituted $(C_6-C_{10})$aryl, $(C_6-C_{10})$aryl-$(C_1-C_{10})$alkyl wherein the aryl moiety is optionally substituted.

The reaction of the aldehyde I with the compound of formula II is preferably carried out in a solvent, the concentration of the reagents I and II, respectively, preferably being between 0.05M and 2M, better still between 0.1M and 0.5M.

The reaction of the aldehyde I with the compound II may be carried out under stoichiometric conditions. However, it is preferable to work in the presence of a slight excess of the compound of formula II, the molar ratio of the compound of formula II to the compound I generally varying between 1 and 3, for example between 1 and 1.5.

The solvent used in this step is selected so as to solubilise both the compound of formula I and the compound of formula II.

The preferred solvents are the aprotic solvents, and especially the optionally halogenated aromatic hydrocarbons (such as benzene, toluene and their chloro derivatives), acetonitrile and the amides of the dimethylformamide and dimethylacetamide type. In some cases, the work may also be done in N-methyl-2-pyrrolidinone as solvent. However, it should be understood that optionally chlorinated aromatic hydrocarbons, such as toluene, are the preferred solvents.

The reactivity of the compounds of formula II varies depending on the meanings of E and G. When E and G both denote a group —$NR_o$, the values of $R_0$ being identical or different (preferably identical), the compound of formula II is highly reactive. The reaction of this compound with the compound of formula I may therefore be carried out under relatively mild operating conditions and especially in the absence of any catalyst.

During the reaction of the aldehyde I with the compound of formula II, the reaction temperature is generally between 15 and 150° C., When E and G denote —$NR_o$— in formula II, a temperature between 15 and 35° C. is generally sufficient.

Conversely, when E and G denote an oxygen atom in the compound of formula II, the reaction of the compound II with the compound I may require harsher reaction conditions.

Thus, in this case, a reaction temperature of between 40 and 120° C. will be more desirable. Moreover, the presence of an inorganic or organic acid catalyst is recommended.

Examples of such catalysts include especially paratoluenesulphonic acid, sulphuric acid, hydrochloric acid or acetic acid, paratoluenesulphonic acid being clearly preferred. However, the skilled man may use any of the acid catalysts generally used in the art for reactions of acetalisation. As a general rule, the acid catalyst is used in an amount of from 0.01 mol to 0.2 mol of catalyst per 1 mol of the aldehyde of formula I, preferably from 0.03 to 0.06 mol of catalyst.

When carrying out step a) it may be advantageous to eliminate the water from the reaction medium as it is formed. To do this, the skilled man may use any one of the methods known in the art. He may, for example, add a drying agent (molecular sieve or aluminium oxide) to the reaction medium.

The second step of the process of the invention consists in separating, by a suitable method, the two diastereoisomers of formula III obtained. To do this, the skilled man may use any one of the methods known in the art.

The separation of the diastereoisomers may be carried out by chromatography or by crystallisation, using the differences in solubility between the two diastereoisomers. However, any other method of separation based on a difference in the physico-chemical properties (such as boiling points, melting points, densities or refractive indices) of the two diastereoisomers of formula III may be used.

When the method of separation used is recrystallisation, the recrystallisation solvent chosen depends on the nature of the different substituents $R_1$ to $R_6$, Z and n, on the one hand, E, G and $A_1$ to $A_4$, on the other hand, and of the diastereoisomer in question. By way of example, when the compound of formula II is 1,2-diphenylethanediol and the compound of formula I is such that $R_1=R_2=R_3=R_6$=phenyl, $R_4=R_5$=H and n=0, the recrystallisation solvent is a mixture of toluene/hexane for one diastereoisomer and dichloromethane in the case of the other diastereoisomer.

When the method of separation is chromatography on a silica column, the eluant is judiciously chosen-so that-the retention times of each of the two diastereoisomers are sufficiently distinct from one another. The two diastereoisomeric acetals obtained by reacting 1,2-diphenylethanediol with the compound of formula I wherein $R_1=R_2$=H; $R_4=R_5=CH_3$; $R_3=R_6$=phenyl and n=0 are thus separated by chromatography on silica gel using a mixture of hexane and dichloromethane as eluant.

The technique of separation by chromatography is described particularly in the work by A. Bertheillier published by Editions Dunod and entitled "Chromatagraphie" (Paris, 1997).

Step c) of the process claimed is carried out separately starting from each of the two diastereoisomers isolated. In this step, the acetal function of each diastereoisomer of formula III is hydrolysed in an acid medium, leading to the corresponding aldehyde of formula I.

This step may be carried out under the conventional conditions of hydrolysis of acetal functions. The hydrolysis is generally carried out by the action of hydrobromic, hydriodic, hydrochloric, periodic or dilute sulphonic acid. It is also possible to envisage hydrolysing the acetal function in the presence of one of the above acids impregnated on silica, and especially in the presence of hydrochloric acid impregnated on silica.

Another method consists in carrying out the hydrolysis by the action of $(CH_3)_3SiI$ in dichloromethane or chloroform, or by the action of $LiBF_4$ in damp acetonitrile.

According to a preferred embodiment of the invention, the reaction of hydrolysing the acetal III is carried out in acetone as solvent. In fact, when the work is done in acetone, the reaction of hydrolysing the acetal (which is a reaction of equilibrium) is shifted towards the formation of the aldehyde I as a result of the concomitant formation of an acetal by the action of the compound of formula II released

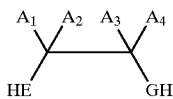

II with the acetone.

Advantageously, this reaction of-exchange is carried out in the presence of hydrochloric acid impregnated on silica. As a general rule, it is sufficient to work in the presence of 3 to 5 mol-% of acid based on the total quantity of acetal of formula III.

According to another aspect, the invention relates to a compound of formula I as hereinbefore defined, wherein n denotes 0, namely a compound of formula A:

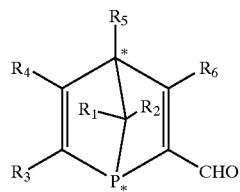

wherein $R_1$, $R_4$, $R_5$ and $R_6$, which may be identical or different, denote a hydrogen atom; a saturated or unsaturated, optionally substituted aliphatic hydrocarbon radical having 1 to 40 carbon atoms, wherein the hydrocarbon chain is optionally interrupted by a heteroatom; an optionally substituted saturated, unsaturated or aromatic carbocyclic or heterocyclic, monocyclic or polycyclic radical; or a saturated or unsaturated aliphatic hydrocarbon radical wherein the hydrocarbon chain is optionally interrupted by a heteroatom and carries a carbocyclic or heterocyclic-radical as hereinbefore defined, said radical optionally being substituted;

or $R_4$ and $R_5$ together with the carbon atoms which carry them form an optionally substituted, saturated or unsaturated, carbocyclic monocycle preferably having 5 to 7 carbon atoms;

$R_2$ denotes a hydrogen atom or the radical X;

$R_3$ denotes the radical X or the radical Y;

with the proviso that one and only one of the substituents $R_2$ and $R_3$ denotes the radical X;

X being selected from among an aromatic carbocyclic or heterocyclic monocyclic or bicyclic radical having 2 to 20 carbon atoms ; a 1-alkenyl radical optionally having one or more additional unsaturated bonds in the hydrocarbon chain and having 2 to 12 carbon atoms; a 1-alkynyl radical optionally having one or more additional unsaturated bonds in the hydrocarbon chain and having 2 to 12 carbon atoms ; a —CN; [($C_1$–$C_{12}$)alkoxy]carbonyl and [($C_6$–$C_{18}$)aryloxy]carbonyl radical; and Y having any of the meanings for $R_1$ with the exception of a hydrogen atom.

Preferred compounds of formula A above are those wherein:

$R_1$, $R_4$, $R_5$, $R_6$ independently denote a hydrogen atom or a T radical selected from among:

a saturated or unsaturated aliphatic hydrocarbon radical having 1 to 12 carbon atoms, wherein the hydrocarbon chain is optionally interrupted by a heteroatom selected from among O, N and S;

a monocyclic carbocyclic radical which is saturated or has 1 or 2 unsaturated bonds in the ring, having 3 to 8 carbon atoms;

a saturated or unsaturated bicyclic carbocyclic radical made up of 2 monocycles fused to each other, each monocycle optionally comprising 1 to 2 unsaturated bonds and having 3 to 8 carbon atoms;

an aromatic $C_6$–$C_{10}$ mono- or bicyclic carbocyclic radical;

a 5- to 6-membered saturated, unsaturated or aromatic monocyclic heterocyclic radical having 1 to 3 heteroatoms selected independently from among N, O and S;

a saturated, unsaturated or aromatic bicyclic heterocyclic radical made up of two 5- to 6-membered monocycles fused to each other, each monocycle having 1 to 3 heteroatoms selected independently from among O, N and S; and a saturated or unsaturated aliphatic hydrocarbon radical having 1 to 12 carbon atoms, wherein the hydrocarbon chain carries a monocyclic carbocyclic or heterocyclic radical as hereinbefore defined, said radical T optionally being substituted;

Y may assume any of the meanings given hereinbefore for $R_1$ with the exception of a hydrogen atom; and X is selected from among a ($C_2$–$C_6$) alkenyl group, a ($C_2$–$C_6$) alkynyl, phenyl, naphthyl, thienyl, furyl, pyrrolyl, imidazolyl, pyrazolyl, thiazolyl, pyridyl, pyrazinyl, pyridazinyl, isothiazolyl, isoxazolyl, benzofuryl, benzothienyl, indolyl, isoindolyl; indolizinyl, indazolyl, purinyl, quinolyl, isoquinolyl, benzothiazolyl and pteridinyl group.

The substituents of the group T are as hereinbefore defined for the compounds of formula I.

A second group of preferred compounds is made up of the compounds of formula A wherein:

$R_1$ and $R_4$ independently denote a hydrogen atom; a ($C_1$–$C_6$)alkyl group; a phenyl group optionally mono- or polysubstituted by ($C_1$–$C_6$)alkyl, ($C_1$–$C_6$)alkoxy, amino, ($C_1$–$C_6$)alkylamino, di($C_1$–$C_6$)alkylamino or a halogen atom; a naphthyl group optionally mono- or polysubstituted by ($C_1$–$C_6$)alkyl, ($C_1$–$C_6$)alkoxy, amino, ($C_1$–$C_6$)alkylamino, di($C_1$–$C_6$)alkylamino or a halogen atom;

$R_5$ denotes a hydrogen atom or a ($C_1$–$C_6$)alkyl group;

$R_6$ denotes a hydrogen atom; a ($C_1$–$C_6$)alkyl group; ($C_3$–$C_8$)cycloalkyl optionally mono- or polysubstituted by ($C_1$–$C_6$)alkyl, ($C_1$–$C_6$)alkoxy, amino, ($C_1$–$C_6$)alkylamino, di($C_1$–$C_6$)alkylamino or a halogen atom; or phenyl optionally mono- or polysubstituted by ($C_1$–$C_6$) alkyl, ($C_1$–$C_6$)alkoxy, amino, ($C_1$–$C_6$)alkylamino, di($C_1$–$C_6$)alkylamino or a halogen atom;

$R_2$ denotes a hydrogen atom or the radical X;

$R_3$ denotes the radical X or the radical Y;

with the proviso that one and only one of the substituents $R_2$ and $R_3$ denotes the radical X;

X denotes a $C_2$–$C_6$ alkenyl group; a $C_2$–$C_6$ alkynyl group; or a phenyl radical; and Y has any of the meanings given hereinbefore for $R_1$ with the exception of a hydrogen atom.

Of these compounds those wherein:

either $R_1$ and $R_2$ denote a hydrogen atom and $R_3$ denotes phenyl optionally mono- or polysubstituted by $(C_1-C_6)$alkyl, $(C_1-C_6)$alkoxy, amino, $(C_1-C_6)$alkylamino, di$(C_1-C_6)$alkylamino or a halogen atom;

or $R_1$ and $R_3$ independently denote phenyl optionally mono- or polysubstituted by $(C_1-C_6)$alkyl, $(C_1-C_6)$alkoxy, amino, $(C_1-C_6)$alkylamino, di$(C_1-C_6)$alkylamino or a halogen atom; and $R_2$ denotes phenyl, are particularly preferred.

The following may be mentioned as particularly preferred compounds:

2-formyl-3,6-diphenyl-4,5-dimethyl-1-phosphanorborna-2,5-diene;

2-formyl-3,6,7,7-tetraphenyl-1-phosphanorbornadiene.

The compounds of formula A above (formula I wherein n denotes 0) may be prepared simply by carrying out a two-step process.

When a compound of formula I is to be prepared wherein n denotes 0, $R_1$, and $R_3$ are other than a hydrogen atom and $R_2$ denotes X as defined for formula I, this process, which is a further object of the invention, comprises the following steps:

a2) reacting a phosphole of formula IV

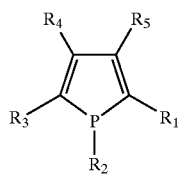

wherein $R_1$, $R_3$, $R_4$ and $R_5$ are as defined for formula I, with the proviso that neither of the groups $R_1$ and $R_3$ denotes a hydrogen atom, and $R_2$ denotes X as defined for formula I, with a compound of formula V

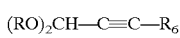

(RO)$_2$CH—C≡C—R$_6$  V wherein $R_6$ is as hereinbefore defined for formula I and R is a $(C_1-C_6)$alkyl group, at a temperature between 100 and 200° C., preferably between 130 and 180° C., to obtain a compound of formula VI

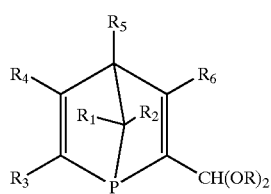

wherein R is a $(C_1-C_6)$alkyl group and $R_1$ to $R_6$ are as hereinbefore defined; and b2) hydrolysing the acetal function of the compound of formula VI thus obtained in an acid medium in order to regenerate the aldehyde function, so as to obtain a compound of formula I.

The first step (step a2) involves first of all a sigmatropic reaction of the order [1,5], followed by a Diels Alder-type reaction of addition.

This step may be diagrammatically shown as follows (with the proviso that $R_2 \neq H$)

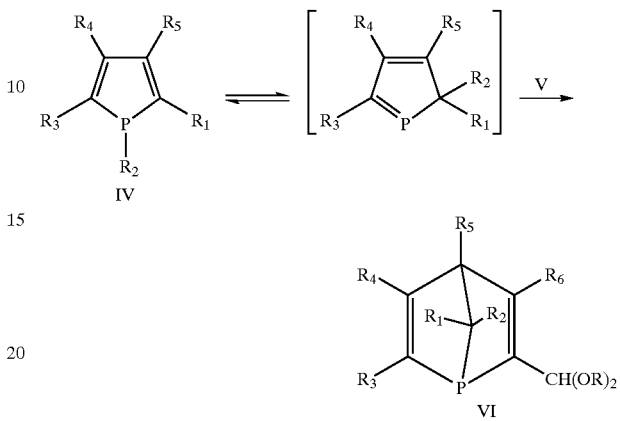

Carrying out the first step requires the reaction medium to be heated to a temperature of between 160 and 190° C., preferably between 130 and 180° C. It is desirable not to heat it above 200° C. so as to avoid the formation of by-products.

The reaction may be carried out without a solvent or in the presence of a solvent. In the latter case, the solvent is preferably an aliphatic, cyclic or aromatic hydrocarbon. Examples of aliphatic or cyclic hydrocarbons include hexane, heptane, octane, nonane, decane, undecane, dodecane, tetradecane or cyclohexane. Examples of aromatic hydrocarbons are benzene, toluene, xylenes, cumene, petroleum fractions made up of a mixture of alkylbenzenes, especially fractions of the Solvesso® type.

The preferred solvents are toluene and xylenes. Mixtures of these solvents may also be used.

However, according to a particularly preferred embodiment, the reaction of the phosphole IV with the acetylene compound V takes place in the absence of a solvent.

The reaction of IV with V is stoichiometric. However, it may be advantageous to use a slight excess of the acetylene V. Generally, the molar ratio of compound V to compound IV varies between 1 and 1.5, preferably between 1 and 1.2.

The second step of the process (step b2) consists in hydrolysing the acetal function of the compound of formula VI obtained in the previous step.

The hydrolysis is carried out according to the invention in an acid medium, by carrying out any of the processes known in the art.

This reaction may for example be carried out under the conditions described hereinbefore, for step c) of the resolution process according to the invention.

According to a preferred embodiment, the hydrolysis of the acetal VI is carried out in an aliphatic halohydrocarbon (such as those defined above and especially dichloromethane) in the presence of hydrochloric acid impregnated on silica.

When a compound of formula I is to be prepared wherein n denotes 0, $R_3$ denotes X as defined for formula I and $R_2$ denotes a hydrogen atom, the process comprises the following steps:

a3) reacting a phosphole of formula VII

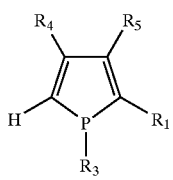

wherein $R_1$, $R_4$ and $R_5$ are as hereinbefore defined for formula I, and
$R_3$ denotes X as defined for formula I,
with a compound of formula V

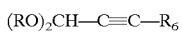

wherein $R_6$ is as defined for formula I and R denotes ($C_1$–$C_6$)alkyl, at a temperature between 100 and 200° C., preferably between 120 and 160° C. so as to obtain a compound of formula VI

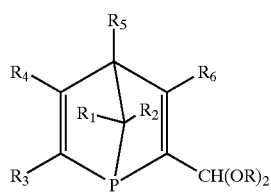

wherein $R_1$ to $R_6$ are as hereinbefore defined, R denotes a ($C_1$–$C_6$)alkyl group; and b3) hydrolysing the acetal function of the compound of formula VI obtained, in an acid medium, in order to regenerate the aldehyde function, so as to obtain a compound of formula I.

The reactions used in steps a3) and b3) may be diagrammatically shown as follows:

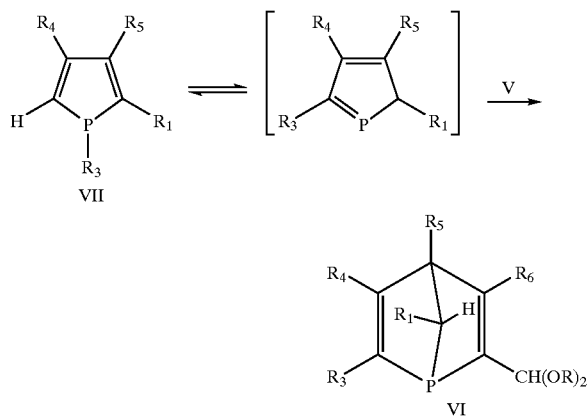

The conditions for performing the reaction a3) are identical to those used when reacting the acetylenic compound V with the phosphole IV (step a2).

Similarly, the working conditions for the reaction of hydrolysis of the acetal VI obtained at the end of the preceding step a3) are similar to those described above for the hydrolysis of the acetal of formula VI (step b2).

The compounds of formula I wherein n=1 and Z denotes an oxygen atom may be prepared from corresponding compounds of formula I wherein n=0 and Z denotes an oxygen atom.

In fact, the oxidation of the corresponding compounds of formula I wherein n=0 and Z denotes an oxygen atom produces the expected compounds.

For this purpose, a peracid such as meta-chloroperbenzoic acid is preferably used as the oxidising agent.

This reaction is carried out in conventional manner at a temperature between −5 and 15° C., preferably between −5 and 10° C., for example 0° C., in an aliphatic halohydrocarbon such as dichloromethane. However, a co-solvent of the aromatic hydrocarbon type may also be used. Thus, a mixture of toluene and dichloromethane is particularly indicated.

When a compound of formula I is to be prepared wherein n denotes 0, $R_1$ denotes a hydrogen atom, $R_2$ is other than a hydrogen atom and $R_3$ denotes X as defined for formula I, the process comprises the following steps:

a4) reacting a phosphole of formula XVI:

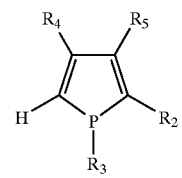

wherein $R_2$, $R_4$ and $R_5$ are as defined for formula I with the proviso that $R_2$ is other-than a hydrogen atom, and $R_3$ denotes X as defined for formula I, with a compound of formula V:

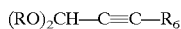

wherein $R_6$ is as defined for formula I and R denotes ($C_1$–$C_6$)alkyl, at a temperature between 100 and 200° C., preferably between 130 and 180° C., so as to obtain a compound of formula VI:

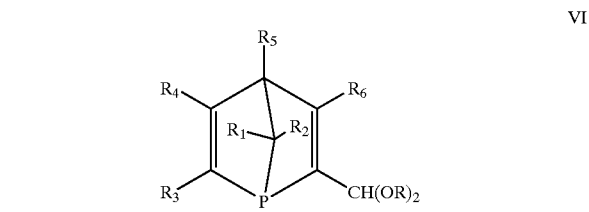

wherein $R_1$ to $R_6$ are as hereinbefore defined, and R denotes a ($C_1$–$C_6$)alkyl group; and b4) hydrolysing the acetal function of the compound of formula VI obtained, in an acid medium, in order to regenerate the aldehyde function, so as to obtain a compound of formula I.

The reactions carried out in step a4) may be shown diagrammatically as follows:

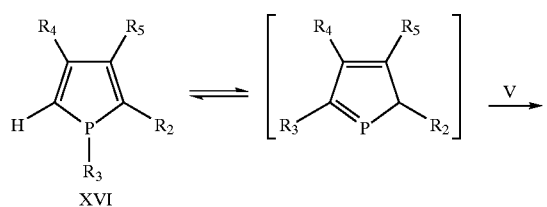

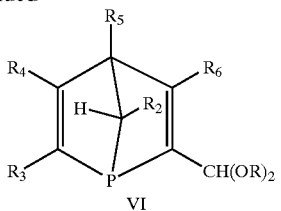

VI

The conditions for carrying out the reactions in steps a4) and b4) are identical to those envisaged in steps a3) and b3).

The compounds of formula I wherein n=1 and Z denotes a sulphur atom may be prepared simply by treating the corresponding compounds of formula I wherein n=0 with sulphur ($S_8$) at a temperature between 50 and 150° C., preferably between 60 and 100° C. for example at 80° C., The reaction is stoichiometric. However, it is preferable to use an excess of sulphur. Thus, the quantity of sulphur $S_8$ is generally between 1 and 3 molar equivalents, for example between 1.8 and 2.5 equivalents.

The sulphuration usually takes place in a hydrocarbon solvent, for example an aliphatic, aromatic or cyclic hydrocarbon as hereinbefore defined. Particularly appropriate conditions are an aromatic hydrocarbon such as toluene, a temperature of 80° C., an inert atmosphere and the use of 2 to 2.5 molar equivalents of $S_8$.

The reaction is generally carried out under atmospheric pressure.

It should be noted that the oxidation and sulphuration of the compounds of formula I in accordance with the processes described above may be carried out directly from the crude products resulting from the coupling of the phosphole IV or VII, respectively, with the acetylene compound V.

In another aspect, the invention relates to the compounds of formula III:

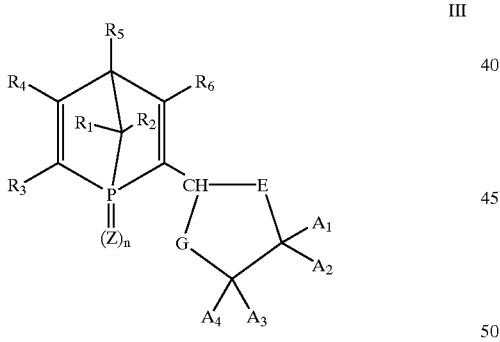

III wherein $R_1$ to $R_6$, X, Y, $A_1$ to $A_4$ are as hereinbefore defined.

Most particularly preferred are the compounds of formula III wherein $R_1$, $R_4$, $R_5$, $R_6$ independently denote a hydrogen atom or a T radical selected from among:
an saturated or unsaturated aliphatic hydrocarbon radical having 1 to 12 carbon atoms, wherein the hydrocarbon chain is optionally interrupted by a heteroatom selected from among O, N and S;
a monocyclic carboxylic radical having 3 to 8 carbon atoms which is saturated or has 1 or 2 unsaturated bonds in the ring;
a saturated or unsaturated bicyclic carbocyclic radical made up of 2 monocycles fused to each other, each monocycle optionally comprising 1 to 2 unsaturated bonds and having 3 to 8 carbon atoms;

a $C_6$–$C_{10}$ aromatic mono- or bicyclic carbocyclic radical a 5- to 6-membered saturated, unsaturated or aromatic monocyclic heterocyclic radical having 1 to 3 heteroatoms selected independently from among N, O and S;
a saturated, unsaturated or aromatic bicyclic heterocyclic radical made up of two 5- to 6-membered monocycles fused to each other, each monocycle having 1 to 3 heteroatoms selected independently from among O, N and S; and
an saturated or unsaturated aliphatic hydrocarbon radical, having 1 to 12 carbon atoms, wherein the hydrocarbon chain carries a monocyclic carbocyclic or heterocyclic radical as hereinbefore defined, said radical T optionally being substituted;

Y may assume any of the meanings given hereinbefore for $R_1$ with the exception of a hydrogen atom; and X is selected from among a ($C_2$–$C_6$) alkenyl group, a ($C_2$–$C_6$) alkynyl, phenyl, naphthyl, thienyl, furyl, pyrrolyl, imidazolyl, pyrazolyl, thiazolyl, pyridyl, pyrazinyl, pyridazinyl, isothiazolyl, isoxazolyl, benzofuryl, benzothienyl, indolyl, isoindolyl; indolizinyl, indazolyl, purinyl, quinolyl, isoquinolyl, benzothiazolyl and pteridinyl group.

A second group of preferred compounds is made up of the compounds of formula III wherein:

$R_1$ and $R_4$ independently denote a hydrogen atom; a ($C_1$–$C_6$)alkyl group; a phenyl group optionally mono- or polysubstituted by ($C_1$–$C_6$)alkyl, ($C_1$–$C_6$)alkoxy, amino, ($C_1$–$C_6$)alkylamino, di($C_1$–$C_6$)alkylamino or a halogen atom; a naphthyl group optionally mono- or polysubstituted by ($C_1$–$C_6$)alkyl, ($C_1$–$C_6$)alkoxy, amino, ($C_1$–$C_6$)alkylamino, di($C_1$–$C_6$)alkylamino or a halogen atom;

$R_5$ denotes a hydrogen atom or a ($C_1$–$C_6$)alkyl group;

$R_6$ denotes a hydrogen atom; a ($C_1$–$C_6$)alkyl group; ($C_3$–$C_8$)cycloalkyl optionally mono- or polysubstituted by ($C_1$–$C_6$)alkyl, ($C_1$–$C_6$)alkoxy, amino, ($C_1$–$C_6$)alkylamino, di($C_1$–$C_6$)alkylamino or a halogen atom; or phenyl optionally mono- or polysubstituted by ($C_1$–$C_6$) alkyl, ($C_1$–$C_6$)alkoxy, amino, ($C_1$–$C_6$)alkylamino, di($C_1$–$C_6$)alkylamino or a halogen atom;

$R_2$ denotes a hydrogen atom or the radical X;

$R_3$ denotes the radical X or the radical Y;

with the proviso that one and only one of the substituents $R_2$ and $R_3$ denotes the radical X;

X denotes a $C_2$–$C_6$ alkenyl group; a $C_2$–$C_6$ alkynyl group; or a phenyl radical; and Y has any of the meanings given hereinbefore for $R_1$ with the exception of a hydrogen atom.

Of these compounds, those wherein:

either $R_1$ and $R_2$ denote a hydrogen atom and $R_3$ denotes phenyl optionally mono- or polysubstituted by ($C_1$–$C_6$) alkyl, ($C_1$–$C_6$)alkoxy, amino, ($C_1$–$C_6$)alkylamino, di($C_1$–$C_6$)alkylamino or a halogen atom;

or $R_1$ and $R_3$ independently denote phenyl optionally mono- or polysubstituted by ($C_1$–$C_6$)alkyl, ($C_1$–$C_6$) alkoxy, amino, ($C_1$–$C_6$)alkylamino, di($C_1$–$C_6$) alkylamino or a halogen atom; and $R_2$ denotes phenyl, are particularly preferred.

The compounds of formula I, in the form of a racemic mixture, or in the form of optically active compounds (as obtained by resolution according to the process of the invention), and the acetals of formula III, in the form of a racemic mixture or in the form of optically active compounds, may be used as ligands in the preparation of catalysts for the hydroformylation of olefins.

It is preferred, for this purpose, to use the compounds of formula I wherein n=0 or those wherein n=1 and Z denotes an oxygen atom.

The hydroformylation of olefins generally produces aldehydes, by the action of carbon monoxide and hydrogen.

By way of example, the hydroformylation of styrene may, depending on the working conditions, produce the following two compounds VIII (branched) and IX (straight-chain) in varying proportions:

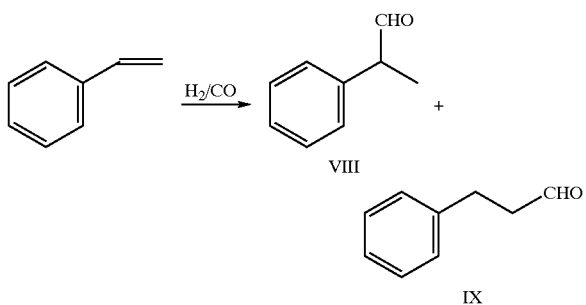

Similarly, the hydroformylation of vinylnaphthalene results in the following aldehyde X (branched) or aldehyde XI (straight-chain), or optionally in a mixture of these two compounds:

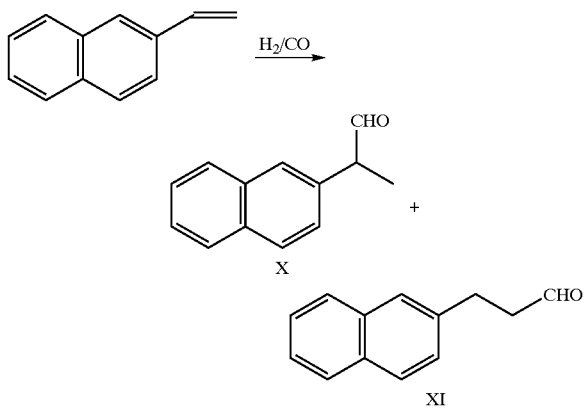

The hydroformylation is carried out at a relatively high pressure (generally above 8MPa) under an $H_2/CO$ atmosphere in the presence of a catalyst which may be a complex of a transition metal (essentially a complex of rhodium, palladium or platinum).

The transition metal complex which is active in the reaction of hydroformylation is generally prepared in situ, during the reaction of hydroformylation starting from a precatalyst, the nature of which varies depending on the transition metal selected.

In the case of hydroformylation with a rhodium complex, the precatalyst may, for example, be one of the following compounds: $[Rh'(CO)_2Cl]_2$; $[Rh'(COD)Cl]_2$ where COD denotes cyclooctadiene; or $Rh'(acac)(CO)_2$ where acac denotes acetyl acetonate.

In this case (rhodium complex), hydroformylation is carried out by (i) mixing the precatalyst with a suitable ligand, for example an optionally optically. active compound of formula I or III, in a solvent; then (ii) adding the olefin substrate (the compound which is to be subjected to the reaction of hydroformylation) to this reaction mixture. The mixture is put under pressure with a gaseous mixture of hydrogen and carbon monoxide, and optionally heated. The general conditions for the hydroformylation of olefins are illustrated in the case of rhodium complexes in J. Am. Chem. Soc. 1997, 119, 4413–4423.

In the case of the compounds of formula I and III according to the invention, $Rh'(acac)(CO)_2$ is preferably used as precatalyst. According to the invention, it is desirable for the optionally optically active phosphine I or III to be present in an excess compared with the precatalyst. Usually, the molar ratio of the ligand of formula I or III to the precatalyst $Rh'(acac)(CO)_2$ varies between 1 and 8, preferably between 3 and 5, and this ratio may be 4, for example.

Suitable solvents include, in particular, the aromatic hydrocarbons such as benzene and toluene; however, to improve the enantioselectivity of the reaction of hydroformylation, an ether (tetrahydrofuran) or a $C_1$–$C_5$ alkanol (methanol) may be chosen as the solvent.

Other suitable solvents are the amides (dimethylformamide or dimethylacetamide) and the $C_4$–$C_5$ ortho-ethers (ethyl orthoformate or methyl orthoformate).

The quantity of solvent used is preferably relatively small, but depends on the nature of the substrate chosen. When the substrate is liquid at ambient temperature, the ratio by volume of the substrate to the solvent may be maintained at between 1 and 4, preferably between 1 and 3. When the substrate is not liquid at ambient temperature, the quantity of solvent used is the amount needed to solubilise the substrate.

The reaction of hydroformylation is carried out under the pressure of a mixture of hydrogen/carbon monoxide, preferably a 1/1 mixture of $H_2/CO$. The pressure generally varies between 8MPa and 16MPa, but a lower pressure may be sufficient. Thus, the pressure may vary from 1 MPa to 20 MPa depending on the circumstances.

It is not always necessary to heat the reaction mixture. However, depending on the nature of the substrate, the nature of the solvent and the catalyst, the work may be done at a reaction temperature between 15° C. and 100° C., preferably between 20° C. and 60° C.

When the hydroformylation is carried out in the presence of a platinum or palladium catalyst, the precatalyst is generally $PdCl_2$, or $PtCl_2$, respectively, and the reaction of hydroformylation is carried out by (i) mixing said precatalyst with tin chloride ($SnCl_2$), a ligand (for example a compound of formula I or a compound of formula III), the substrate (i.e. the compound which is to be subjected to the reaction of hydroformylation) and a solvent; then (ii) putting it under pressure with a mixture of $H_2/CO$ and optionally heating the reaction mixture. The conditions of this type of hydroformylation reaction are illustrated for example in J. Am. Chem. Soc. Vol 119, n° 19, 1997, 4413. Generally, the quantity of tin chloride varies between 1 and 4 molar equivalents, preferably between 1 and 3 molar equivalents in relation to the mols of platinum or palladium, respectively, used. Similarly, for a ligand of formula I or III according to the invention, the molar ratio of the ligand to $PtCl_2$ or $PdCl_2$, respectively, varies between i and 4, preferably between 1 and 3.

The aromatic hydrocarbons, ethers, aliphatic alcohols, amides and ortho-ethers as hereinbefore defined may be used as solvent. However, it is preferable to use the aromatic hydrocarbons of the benzene and toluene type.

As for the temperature and pressure conditions, they are substantially as described above in relation to the hydroformylation of olefins using rhodium.

Other working conditions which may also be used within the scope of the invention are as described in J. Am. Chem. Soc. 1987, 109, 7122–7127.

The compounds of formula I and III according to the invention are particularly useful as ligands for the preparation of catalysts which may be used in the hydroformylation of olefins from the point of view of the activity and regioselectivity of the hydroformylation reactions. In the presence of a catalyst of this kind, the reaction of hydroformylation results in a predominant aldehyde which is either the branched compound or the expected straight-chain compound.

Moreover, the inventors have noted that, astonishingly, the catalysts prepared from the compounds of formula I or III according to the invention make it possible for olefins to be successfully hydroformylated while at the same time the aldehyde formed is acetalised.

Thus, the inventors have succeeded in carrying out the following reaction starting from styrene, and have observed the formation of the acetal XIII, as the major reaction product:

2—Preparation of 3,6-Diphenyl-4,5-dimethyl-2-formyl-1-phosphanorborna-2,5-diene of Formula (Compound 1):

3 g of silica, 5 ml of $CH_2Cl_2$ and 1 ml of HCl (11N) are placed in a flask. To this suspension is added, at ambient temperature, over a period of 5 min., the crude product obtained in the previous step dissolved in 10 ml of $CH_2Cl_2$. The medium is stirred for 15 minutes and the mixture is then filtered through a frit, then the solvent is evaporated. The product is then chromatographed on a silica column (Eluant: $CH_2Cl_2$).

The title product is obtained in the form of a yellowish solid (melting point: 112° C.; 3.8 g; yield: 88%).

$^1$H NMR (CDCl$_3$) δ (ppm)=1.4 (3H, s, CH$_3$); 2.1 (3H, s, CH$_3$); 2.2 (2H, m, CH$_2$); 7.3 (10H, m, aromatic CH); 9.7 (1H, d, $^3$J(P-H)=9.2 Hz, CHO). $^{31}$P NMR(CDCl$_3$) δ (ppm)=−31.2 ppm. $^{13}$C NMR (CDCl$_3$) δ (ppm)=16.5 (CH$_3$, s); 20.4 (CH$_3$, s); 65.1 (CH$_2$, s); 73.6 (Cq, d, $^1$J(P-C)=5.9 Hz); 129.0–156 (sp2 carbons); 191.0 (CHO, d, $^2$J(P-C)=16.7 Hz).

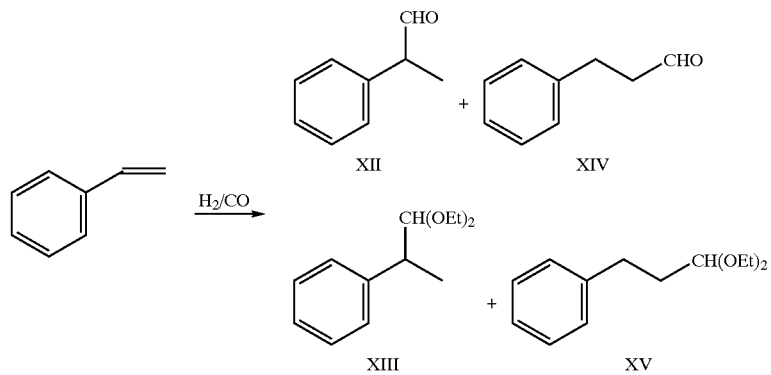

This result is all the more surprising as Castillon et al. showed, in Tetrahedron Letters, 1994, 35, 2361–2364, that this reaction of hydroformylation-transacetalisation did not occur, in the absence of acid catalysis, in spite of the use of catalysts consisting of rhodium/P(Ph)$_3$ complexes, in the presence of pyridinium p-toluenesulphonate.

The following examples illustrate the invention more precisely.

PREPARATION 1

3,6-Diphenyl-4,5-dimethyl-2-formyl-1-phosphanorborna-2,5-diene (I: n=0; R$_1$=R$_2$=H; R$_4$=R$_5$=—CH$_3$; R$_3$=R$_6$=—C$_6$H$_5$)-Compound 1

1—Preparation of the Diethyl Acetal of 3,6-Diphenyl-4,5-dimethyl-2-formyl-1-phosphanorborna-2,5-diene of Formula

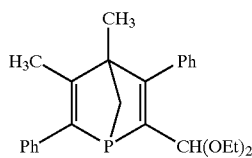

A mixture of 3,4-dimethyl-1-phenyl phosphole (13.3 mmol, 2.5 g) and phenylpropargyl diethyl acetal aldehyde (13.3 mmol, 2.7 g) is heated to 140° C. for 4 hours in a flask. The crude reaction product is obtained in the form of a deep brown oil, after which the product is used without purification.

Analysis calculated for C$_{21}$H$_{19}$OP: C:79.25; H:6.01; P:9.70. Found C:78.62; H:6.14; P:9.62. Mass spectrum: M$^+$(318,10%); M$^+$−C$_9$H$_6$O(188,100%).

PREPARATION 2

3,6,7,7-Tetraphenyl-2-formyl-1-phosphanorborna-2,5-diene (I: n=0; R$_1$=R$_2$=R$_3$=R$_6$=—C$_6$H$_5$; R$_4$=R$_5$=H)-Compound 2

1—Preparation of the Diethyl Acetal of 3,6,7,7-tetraphenyl-2-formyl-1-phosphanorborna-2,5-diene, of Formula:

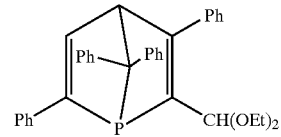

A mixture of 1,2,5-triphenylphosphole (4.9 g, 15.9 mmol) and phenylpropargyl diethyl acetal aldehyde (3.2g, 15.9 mmol) is heated to 170–180° C. in a flask for 8 days. The crude reaction product is obtained in the form of a deep brown oil. The crude product is then used without any purification.

2—Preparation of 3,6,7,7-tetraphenyl-2-formyl-1-phosphanorborna-2,5-diene (Compound 2):

3 g of silica, 5 ml of $CH_2Cl_2$ and 1 ml of HCl (11N) are placed in a flask. To this suspension is added, at ambient temperature, over a period of 5 min., the crude product obtained in the previous step dissolved in 10 ml of $CH_2Cl_2$.

The product is obtained in the form of a white solid (melting point: 234° C., yield: 45%).

$^1$H NMR (CDCl$_3$) δ (ppm)=5.4 (1H, m, CH); 7.26 (21H, m, CH); 9.7 (1H, d, J=9.2 Hz, CHO). $^{31}$P NMR (CDCl$_3$) δ (ppm)=−0.3 ppm. $^{13}$C NMR (CDCl$_3$) δ (ppm)=71.6 (CH,d, J=5.6 Hz); 88.2 (Cq, s); 128–181 (sp$_2$ carbons); 190.3 (CHO, d, $^2$J=16.5 Hz). Analysis calculated for C$_{31}$H$_{23}$OP: C:84.14; H:5.24; P:7.00. Found C:81.54; H:5.21; P:7.31. Mass spectrum m/z (relative intensity): 486 (M$^+$,40), 165 (M$^+$−C$_{18}$H$_{14}$OP, 100).

EXAMPLE 1

Resolution of Compound 1 of Preparation 1
1—Formation of an Acetal by the Action of 2-Hydroxy-1,2-diphenylethanol: Compound 3

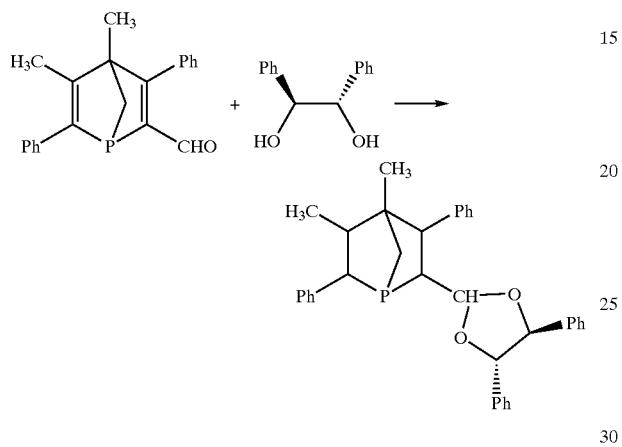

0.7 g of compound 1 obtained in preparation 1 (M=318 g/mol, 2.2 mmol), 0.5 g of (S,S) 2-hydroxy-1,2-diphenylethanol (M=214 g/mol, 2.2 mmol), 0.01 g of p-toluenesulphonic acid and 7 ml of toluene are placed in a flask provided with a bar magnet. The mixture is heated to the reflux temperature of the toluene for 3 hours. The progress of the reaction is monitored by $^{31}$P NMR.

The product obtained is a mixture of two diastereoisomers (compounds 3A and 3B).

2—Separation of the Diastereoisomers

The two diastereoisomers are separated by flash chromatography on silica gel using a 7/3 mixture of hexane/CH$_2$Cl$_2$.

Diastereoisomer A: Compound 3A

[a]$_D$=+41.6°. $^1$H NMR (CDCl$_3$) δ (ppm)=1.4 (3H, s, CH$_3$); 2.0 (3H, s, CH$_3$); 2.3 (4H, m, CH$_2$); 4.7 (1H, d, $^1$J(H-H)=8.0 Hz); 5,1 (1H, d, $^1$J(H-H)=8.0 Hz); 5.9 (1H, d, $^3$J(P-H)=8,7 Hz); 6.9–7.5 (10H, m, aromatic CH). $^{31}$P NMR (CDCl$_3$)δ (ppm)=−22.9. $^{13}$C NMR (CDCl$_3$)δ (ppm)=16.4 (CH$_3$, s); 21.0 (CH$_3$, s); 66.9 (Cq, s); 71.8 (CH$_2$, d, $^2$J(P-C)=6.0 Hz); 87.0 (CH, d, $^2$J(P-C)=69.8 Hz); 103.0 (CH, d,$^4$J(P-C)=15.3 Hz); 129.0–169.0 (sp$_2$ carbons).

Diastereoisomer B: Compound 3B

[a]$_D$=+200°. $^1$H NMR (CDCl$_3$) δ (ppm)=1.5 (3H, s, CH$_3$); 2.2 (3H, s, CH$_3$); 2.3 (4H, m, CH$_2$); 5.0 (1H, d, $^1$J(H-H)=8.0 Hz); 5.2 (1H, d, $^1$J(H-H)=8.0 Hz); 6.0 (1H, d, $^3$J(P-H)=9.0 Hz); 6.9–7.5 (20H, m, aromatic CH). $^{31}$P NMR (CDCl$_3$) δ (ppm)=−22.1. $^{13}$C NMR (CDCl$_3$) δ (ppm)=16.2 (CH$_3$, s); 20.9 (CH$_3$, s); 66.4 (Cq, s); 71.8 (CH$_2$, d, $^2$J(P-C)=6.0 Hz); 87.2 (CH, d, $^2$J(P-C)=88.3 Hz); 102.6 (CH, d, $^4$J(P-C)=15.4 Hz); 129.0–169.0 (sp$_2$ carbons).

3—Hydrolysis of the Acetal 3 g of silica, 5 ml of dichloromethane and 1 ml of HCl (11N) are placed in a flask, with stirring. To this suspension is added, at ambient temperature, over a period of 5 min., the compound 3A isolated in step 2 above and dissolved in 10 ml of CH$_2$Cl$_2$. The mixture is stirred for 15 minutes, then filtered through a frit and the solvent is evaporated.

The product is then chromatographed on a silica column using CH$_2$Cl$_2$ as eluant. The expected aldehyde is obtained in the form of a yellowish solid.

The aldehyde obtained (compound 5A) is characterised by a rotatory power [a]$_D$=+134.5°, measured at 20° C. in CDCl$_3$ with c=0.55.

Using the same method as described above but starting from the compound 3B, the corresponding aldehyde 5B is obtained, which is characterised by a rotatory power [a]$_D$32 −133°, measured at 20° C. in CDCl$_3$ with c=0.55.

EXAMPLE 2

Resolution of Compound 2 of Preparation 2
1—Formation of an Acetal by the Action of 2-Hydroxy-1,2-diphenyl Ethanol: Compound 4

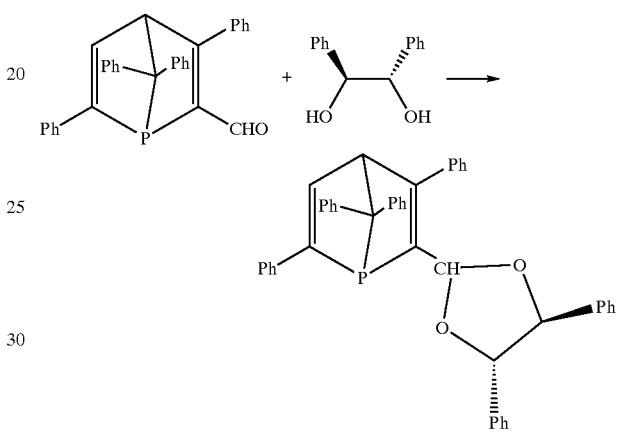

206 mg of compound 2 of preparation 2 are heated to 50° C. in 10 ml of toluene, in a flask, under argon, for 5 h, in the presence of 100 mg of (S,S)-(−)-2-hydroxy-1,2-diphenylethanol and 1 mg of p-toluenesulphonic acid. The solvent is then evaporated off. The product obtained is a mixture of two diastereoisomers.

2—Separation of the Diastereoisomers

The crude reaction product obtained in step 1 is taken up in an 80/20 mixture of toluene/hexane.

One of the two diastereoisomers is precipitated. It is filtered, and washed with toluene, then recrystallised from a 70/30 mixture of toluene/hexane. The mother liquors are concentrated and the second diastereoisomer is crystallised from a CH$_2$Cl$_2$ mixture.

Diastereoisomer A: Compound 4A

[a]$_D$=−119.6°(c=2.7; CDCl$_3$). $^1$H NMR (CDCl$_3$) δ (ppm)= 4.6 (1H, d, J=8.1 Hz, CH); 5.0 (1H, d, J=8,1 Hz, CH); 5.2 (1H, m, CH); 6.0 (1H, d, J=9.7 Hz, CH), 7–7.6 (30H, m, arom. CH). $^{31}$P NMR (CDCl$_3$) δ (ppm)=7.8 ppm. $^{13}$C NMR (CDCl$_3$)δ (ppm)=70.1 (d, $^2$J(P-C)=5.3 Hz, CH); 87.3(s, CH); 102.1 (d, $^4$J(C-P)=15.6 Hz, CH);126–164 (sp$_2$ carbons).

Analysis calculated for C$_{45}$H$_{35}$O$_2$P: C:84.61; H:5.52; P:4.85; O:5.00. Found C:84.41; H:5.55; P:5.1.

Diastereoisomer B: Compound 4B

[a]$_D$=−94°(c=1,0; CDCl$_3$). $^1$H NMR (CDCl$_3$) δ (ppm)= 4.6 (1H, d, J=8.0 Hz, CH); 5.1 (1H, d, J=8.0 Hz, CH); 5.2 (1H, m, CH); 6.0 (1H, d, J=9.8 Hz, CH), 7–7.6 (30H, m, arom CH). $^{31}$P NMR (CDCl$_3$) δ (ppm)=6.7 ppm. $^{13}$C NMR (CDCl$_3$) δ (ppm)=71.0 (d, $^2$J(C-P)=5.7 Hz, CH); 86.8(s, CH); 102.7 (d, $^4$J(C-P)=15.3 Hz, CH); 126–164 (sp$_2$ carbons).

3—Hydrolysis of the Acetal

The acetal 4A is hydrolysed to form the aldehyde 6A by carrying out a method identical to that in Example 1.3.

The rotatory power of the aldehyde 6A measured at 20° C. in $CDCl_3$ with c=0.41 is $[a]_D=+90°$.

Similarly, starting with the acetal 4B, the aldehyde 6B is obtained, the rotatory power of which is $[a]_D=-91°$, measured at +20° C. in $CDCl_3$ with c=0.41.

EXAMPLE 3

Reaction of Hydroformylation of Styrene Catalysed by a Rhodium Complex

1—Hydroformylation of Styrene

In this example, the catalytic activity of various rhodium catalysts prepared from different ligands was studied.

In every case, the hydroformylation of the styrene is effected as follows:

$Rh(acac)(CO)_2$ (2.58 mg; 0.01 mmol), 1 ml of solvent (toluene, THF, MeOH or DMF), a ligand (1 to 4 eq), followed by 2 ml of styrene are placed in a 25 ml glass flask under argon. Then a mixture of hydrogen/carbon monoxide (1/1) is added until the operating pressure is reached. The reaction medium is stirred and heated, if necessary.

The exact working conditions (temperature, pressure, solvent, ligand and relative ratio of the ligand and precatalyst) are as shown in the Table which follows.

| | | Working Conditions | | | | |
|---|---|---|---|---|---|---|
| Example no | Ligand | T (° C.) | t[1] (h) | P (MPa) | Solvent | Rh/P[2] |
| 3.1 | Compound 1[3] | 50 | 23 | 10 | toluene | 1/2 |
| 3.2 | Compound 1[3] | 20 | 41 | 15 | THF | 1/2 |
| 3.3 | Compound 5A[4] | 20 | 19 | 10 | MeOH | 1/4 |
| 3.4 | Compound 3A[4] | 40 | 19 | 10 | MeOH | 1/4 |
| 3.5 | Compound 4A[4] | 20 | 21 | 15 | THF | 1/2 |
| 3.6 | Compound 4A[4] | 40 | 19 | 10 | MeOH | 1/4 |
| 3.7 | Compound 4B[4] | 40 | 19 | 10 | MeOH | 1/4 |
| 3.8 | Compound 2[3] | 20 | 19 | 10 | MeOH | 1/4 |
| 3.9 | Compound 3B | 40 | 19 | 10 | MeOH | 1/4 |

[1]duration of the reaction
[2]ratio of the number of molar equivalents of rhodium to the number of phosphorus equivalents
[3]racemic mixture
[4]optically active diastereoisomer At the end of the reaction, the ratio of the straight-chain compound (phenylpropaldehyde) to the branched compound (hydratropaldehyde) of formula:

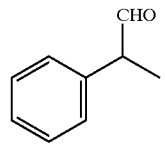

is determined by $^1H$ NMR of the crude reaction product (reaction mixture as it is). The styrene and the solvent are then evaporated under reduced pressure. The hydratropaldehyde is then distilled in a ball oven under reduced pressure at 90–100° C. 50 mg of the distilled product are then dissolved in 5 ml of toluene, then the rotatory power of the solution is measured.

2. Results

The results obtained are assembled in the following Table.

| Example No | Ligand | b/s[1] | FR[2] (h$^{-1}$) | TT %[3] | $\alpha^{(4)}$ D |
|---|---|---|---|---|---|
| 3.1 | Compound 1 | 94/6 | 91 | 100 | — |
| 3.2 | Compound 1 | 95/5 | 23 | 47 | — |
| 3.3 | Compound 5A | 99/1 | 10 | 10 | +10 |
| 3.4 | Compound 3A | 95/5 | 105 | 100 | — |
| 3.5 | Compound 4A | 98/2 | 41 | 43 | — |
| 3.6 | Compound 4A | 97/3 | 76 | 73 | — |
| 3.7 | Compound 4B | 96/4 | 52 | 50 | — |
| 3.8 | Compound 2 | 97/3 | 105 | 100 | — |
| 3.9 | Compound 3B | 95/5 | 52 | 50 | — |

In example 3.3, the hydroformylation was enantioselective (1) b/s: molar ratio of the branched product to the straight-chain product
(2) FR denotes the rotation frequency which is the following ratio:

$$\frac{\text{number of mols of substrate converted}}{\text{number of mols of catalyst} \times \text{time (h)}}$$

(3) conversion level
(4) rotatory power measured at 20° C. in $CDCl_3$ with c=1.

This Table clearly shows that the catalysts according to the invention have an excellent activity. Similarly, these tests confirm that the regioselectivity obtained in the presence of the catalysts of the invention is high.

EXAMPLE 4

Reaction of Hydroformylation of N-Vinylphthalamide Catalysed by a Rhodium Complex $Rh(acac)(CO)_2$ (2.58 mg; 0.01 mmol), 1 ml of toluene, followed by the ligand (1 to 4 eq) and N-vinylphthalamide dissolved in 2 to 3 ml of toluene are placed in a 25 ml glass flask under argon. Then a mixture of hydrogen/carbon monoxide (1/1) is added until the operating pressure is reached. The reaction medium is stirred and heated, if necessary.

At the end of the reaction the solvent is evaporated and the rotatory power is measured from the crude product.

| Example no | Ligand | T (° C.) | t[1] (h) | solvent | Rh/P[2] | P (MPa) |
|---|---|---|---|---|---|---|
| 4.1 | Compound 4A[3] | 20 | 41 | toluene | 1/1 | 10 |
| 4.2 | Compound 4A[3] | 20 | 36 | toluene | 1/2 | 2 |

[1]duration of the reaction
[2]ratio of the number of molar equivalents of rhodium to the number of phosphorus equivalents
[3]optically active diastereoisomer.

The results obtained are as shown below.

| Example n° | Ligand | b/s[1] | TT%[2] | $\alpha_D^{(3)}$ |
|---|---|---|---|---|
| 4.1 | Compound 4A | 100 | 70 | — |
| 4.2 | Compound 4A | 100 | 70 | +13 |

In Example 4.2., the hydroformylation was enantioselective.

(1) b/s: molar ratio of the branched product to the straight-chain product
(2) conversion level
(3) rotatory power measured at 20° C. in CDCl$_3$ with c=1.

EXAMPLE 5

Reaction of Hydroformylation of 2-Vinyinaphthalene Catalysed by a Rhodium Complex The method used in this Example is identical to that in Example 4 except that the substrate used is 2-vinyinaphthalene and not N-vinylphthalamide.

| Example no. | Ligand | T (° C.) | t$^{(1)}$ (h) | P (MPa) | solvent | Rh/P$^{(2)}$ |
|---|---|---|---|---|---|---|
| 5.1 | Compound 5A$^{(3)}$ | 20 | 67 | 15 | toluene | 1/2 |

$^{(1)}$duration of the reaction
$^{(2)}$ratio of the number of molar equivalents of rhodium to the number of phosphorus equivalents
$^{(3)}$optically active diastereoisomer.

The results obtained are as follows.

| Example no. | Ligand | r/l$^{(1)}$ | TT%$^{(2)}$ | α$_D$$^{(3)}$ |
|---|---|---|---|---|
| 5.1 | Compound 5A | 98/2 | 81 | +3,8 |

In Example 5.2, the hydroformylation was enantioselective.

(1) b/s: molar ratio of the branched product to the straight-chain product
(2) conversion level
(3) rotatory power measured at 20° C. in CDCl$_3$ with c=1.

EXAMPLE 6

Reaction of Hydroformylation of Styrene in the Presence of HC(OEt)$_3$ Catalysed by a Rhodium Complex The hydroformylation of the styrene is carried out using a method identical to that in Example 3 except that 1 ml of HC(OEt)$_3$ is used as solvent.

| Example no. | Ligand | T (° C.) | P (MPa) | t$^{(1)}$ (h) | solvent | Rh/P$^{(2)}$ |
|---|---|---|---|---|---|---|
| 6.1 | Compound 4A$^{(3)}$ | 20 | 10 | 19 | HC(OEt)$_3$ | 1/4 |

$^{(1)}$duration of the reaction
$^{(2)}$ratio of the number of molar equivalents of rhodium to the number of phosphorus equivalents
$^{(3)}$optically active diastereoisomer.

The results obtained are as shown in the following Table.

| Example no. | Ligand | % D$^{(1)}$ | % XII | % XIII | % XIV | % XV |
|---|---|---|---|---|---|---|
| 6.1 | Compound 4A | 0 | 63 | 35 | 0 | 2 |

$^{(1)}$D = starting styrene with the proviso that the compounds of formula XII, XII, XIV and XV are as follows:

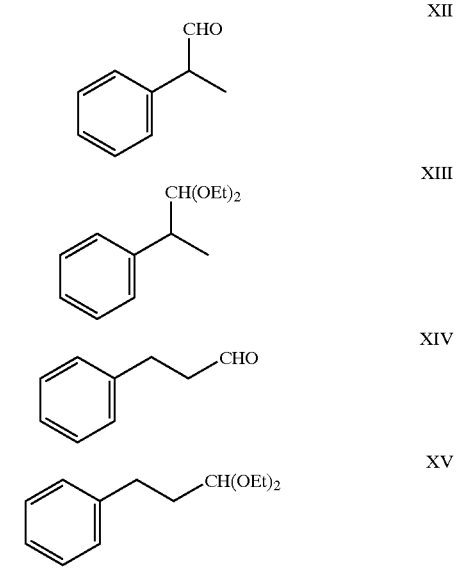

What is claimed is:
1. Process for resolving a racemic mixture of enantiomers of aldehydes of formula I:

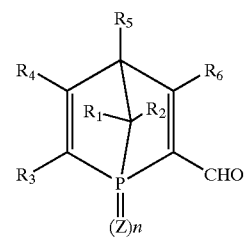

wherein
R$_1$, R$_4$, R$_5$ and R$_6$, are independently selected from the group consisting of hydrogen; a saturated or unsaturated, optionally substituted, aliphatic hydrocarbon having 1 to 40 carbon atoms, wherein the hydrocarbon chain of the hydrocarbon is optionally interrupted by a heteroatom; an optionally substituted carbocyclic or heterocyclic, saturated, unsaturated or aromatic monocyclic or polycyclic group; and an aliphatic saturated or unsaturated hydrocarbon wherein the hydrocarbon is substituted with an optionally substituted carbocyclic or heterocyclic group and wherein the hydrocarbon chain of the hydrocarbon is optionally interrupted by a heteroatom;
or R$_4$ and R$_5$ together with the carbon atoms to which they are attached form an optionally substituted saturated or unsaturated carbocyclic monocyclic group;

Z is sulphur or oxygen;

n is 0 or 1;

$R_2$ is hydrogen or X;

$R_3$ is X or Y;

with the proviso that only one of the substituents $R_2$ and $R_3$ is X;

X is selected from the group consisting of an aromatic monocyclic or bicyclic carbocycle or heterocycle having 2 to 20 carbon atoms; a 1-alkenyl optionally having one or more additional unsaturated bonds in the hydrocarbon chain of the alkenyl and having 2 to 12 carbon atoms; 1-alkynyl optionally having one or more additional unsaturated bonds in the hydrocarbon chain of the alkynyl and having 2 to 12 carbon atoms; —CN; carbonyl; and carbonyl; and Y is selected from the group consisting of a saturated or unsaturated, optionally substituted, aliphatic hydrocarbon having 1 to 40 carbon atoms, wherein the hydrocarbon chain of the hydrocarbon is optionally interrupted by a heteroatom; an optionally substituted carbocyclic or heterocyclic, saturated, unsaturated or aromatic monocyclic or polycyclic group; and an aliphatic saturated or unsaturated hydrocarbon wherein the hydrocarbon is substituted with an optionally substituted carbocyclic or heterocyclic group and wherein the hydrocarbon chain of the hydrocarbon is optionally interrupted by a heteroatom;

said process having the steps consisting of a) reacting said compound of formula I with an optically active compound of formula II:

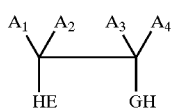

wherein the group $>C(A_1)(A_2)$ is distinct from the group $>C(A_3)(A_4)$;

$A_1, A_2, A_3, A_4$ are independently selected from the group consisting of hydrogen; $(C_1–C_{10})$alkyl; $(C_6–C_{10})$aryl optionally mono- or polysubstituted with $(C_1–C_{10})$alkyl, $(C_1–C_{10})$alkoxy, amino, $(C_1–C_{10})$alkylamino, di$(C_1–C_{10})$alkylamino or halo; a $(C_3–C_8)$cycloalkyl group optionally mono- or polysubstituted with $(C_1–C_{10})$alkyl, $(C_1–C_{10})$alkoxy, amino, $(C_1–C_{10})$alkylamino, di$(C_1–C_{10})$alkylamino or halo; a saturated, unsaturated or aromatic 5- to 7-membered heterocyclic group having 1 to 3 heteroatoms selected from the group consisting of O, N and S, wherein the saturated, unsaturated, or aromatic group is optionally mono- or polysubstituted with $(C_1–C_{10})$alkyl, $(C_1–C_{10})$alkoxy, amino, di$(C_1–C_{10})$alkylamino or halo; or $A_1$ and $A_3$ together with the carbon atoms to which they are attached form a $(C_4–C_8)$ carbocycle, wherein the carbocycle is optionally mono- or polysubstituted with $(C_1–C_{10})$alkyl, $(C_1–C_{10})$ alkoxy, amino, $(C_1–C_{10})$alkylamino, or di$(C_1–C_{10})$alkylamino, or halo; or $A_1$ and $A_3$ together with the carbon atoms to which they are attached form a saturated 5- to 7-membered oxygen containing heterocycle, wherein the heterocycle optionally contains one to two additional heteroatoms independently selected from the group consisting of O, N and S, wherein the heterocycle is optionally mono- or polysubstituted with $(C_1–C_{10})$alkyl, $(C_1–C_{10})$ alkoxy, amino, $(C_1–C_{10})$alkylamino, di$(C_1–C_{10})$ alkylamino, hydroxyl or halo; and E and G independently are oxygen, or a divalent group —$NR_0$— wherein the $R_0$ group independently is hydrogen, $(C_1–C_{10})$alkyl, $(C_6–C_{10})$aryl optionally substituted by $(C_1–C_{10})$alkyl; or $(C_6–C_{10})$aryl-$(C_1–C_{10})$alkyl wherein the aryl moiety is optionally substituted by a $(C_1–C_{10})$alkyl;

wherein the reaction of the compound of formula I and the compound of formula II forms a compound of formula III as a mixture of diastereoisomers

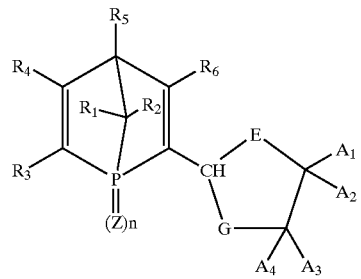

wherein $R_1$ to $R_6$, $A_1$ to $A_4$, E, G, Z and n are as defined above;

b) separating the diastereoisomers of formula III by a suitable method; and c) separately regenerating the aldehyde function of each of the separated diastereoisomers of formula III, by hydrolyzing the acetal function in an acid medium to provide an enantiomerically pure aldehyde of formula I.

2. Process according to claim 1, wherein $R_1$, $R_4$, $R_5$, and $R_6$ independently are hydrogen or a group selected from the group consisting of:

a saturated or unsaturated aliphatic hydrocarbon having 1 to 12 carbon atoms, wherein the hydrocarbon chain is optionally interrupted by a heteroatom selected from the group consisting of O, N and S;

a monocyclic carbocycle which is saturated or has 1 or 2 unsaturated bonds in the ring, wherein the carbocycle has 3 to 8 carbon atoms;

a saturated or unsaturated bicyclic carbocycle made up of 2 monocycles fused to each other, each monocycle optionally comprising 1 to 2 unsaturated bonds and having 3 to 8 carbon atoms;

an aromatic $C_6–C_{10}$ mono- or bicyclic carbocycle;

a saturated, unsaturated or aromatic 5- to 6-membered monocyclic heterocycle having 1 to 3 heteroatoms independently selected from the group consisting of N, O and S;

a saturated, unsaturated or aromatic bicyclic heterocycle made up of two 5- or 6-membered monocycles fused to each other, each monocycle having 1 to 3 heteroatoms independently selected from the group consisting of O, N and S; and a saturated or unsaturated aliphatic hydrocarbon, having 1 to 12 carbon atoms, wherein the hydrocarbon chain is substituted with a monocyclic carbocyclic or heterocyclic group, wherein the group is optionally mono- or polysubstituted with $(C_1-C_6)$alkyl; $(C_2-C_6)$alkenyl; $(C_1-C_6)$alkoxy; $(C_2-C_6)$acyl; —$R_a$—OH, —$R_a$—COO$R_b$, —$R_a$—NO$_2$, —$R_a$—CN—, —$R_a$—N($R_b$)$_2$, —$R_a$—SH, —$R_a$—halo, —$R_a$—CF$_3$—O—CF$_3$ (wherein $R_a$ is a bond or $(C_1-C_6)$alkylene, $R_b$ is independently hydrogen or $(C_1-C_6)$alkyl); or

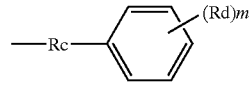

where $R_d$ is selected from the group consisting of $(C_1-C_6)$alkyl; $(C_2-C_6)$alkenyl; $(C_1-C_6)$alkoxy; $(C_2-C_6)$acyl; —$R_a$—OH; —$R_a$—COO$R_b$; —$R_a$—NO$_2$; —$R_a$—CN; —$R_a$—N($R_b$)$_2$; —$R_a$—SH; —$R_a$—halo; —$R_a$—CF$_3$ and —O—CF$_3$ (wherein $R_a$ and $R_b$ are as defined above), m is an integer between 0 and 5;

$R_c$ is a bond; $(C_1-C_6)$alkylene; —O—; —COO—; —N$R_b$—; —S—; —SO$_2$—; where $R_b$ is as defined above;

Y is selected from the group consisting of a saturated or unsaturated, optionally substituted, aliphatic hydrocarbon having 1 to 40 carbon atoms, wherein the hydrocarbon chain of the hydrocarbon is optionally interrupted by a heteroatom; an optionally substituted carbocyclic or heterocyclic, saturated, unsaturated or aromatic monocyclic or polycyclic group; and an aliphatic saturated or unsaturated hydrocarbon wherein the hydrocarbon is substituted with an optionally substituted carbocyclic or heterocyclic group and wherein the hydrocarbon chain of the hydrocarbon is optionally interrupted by a heteroatom; and X is selected from the group consisting of $(C_2-C_6)$alkenyl, $(C_2-C_5)$alkynyl; phenyl, naphthyl, thienyl, furyl, pyrrolyl, imidazolyl, pyrazolyl, thiazolyl, pyridyl, pyrazinyl, pyridazinyl, isothiazolyl, isoxazolyl, benzofuryl, benzothienyl, indolyl, isoindolyl, indolizinyl, indazolyl, purinyl, quinolyl, isoquinolyl, benzothiazolyl and pteridinyl group.

3. Process according to claim 1 or claim 2, wherein $R_1$ and $R_4$ independently are hydrogen; $(C_1-C_6)$alkyl; phenyl optionally mono- or polysubstituted by $(C_1-C_6)$alkyl, $(C_1-C_6)$alkoxy, amino, $(C_1-C_6)$alkylamino, di$(C_1-C_6)$alkylamino or halo; or naphthyl optionally mono- or polysubstituted by $(C_1-C_6)$alkyl, $(C_1-C_6)$alkoxy, amino, $(C_1-C_6)$alkylamino, di$(C_1-C_6)$alkylamino or halo;

$R_5$ is hydrogen or $(C_1-C_6)$alkyl;

$R_6$ is hydrogen; a $(C_1-C_6)$alkyl; $(C_3-C_8)$cycloalkyl optionally mono- or polysubstituted by $(C_1-C_6)$alkyl, $(C_1-C_6)$alkoxy, amino, $(C_1-C_6)$alkylamino, di$(C_1-C_6)$alkylamino or halo; or phenyl optionally mono- or polysubstituted by $(C_1-C_6)$alkyl, $(C_1-C_6)$alkoxy, amino, $(C_1-C_6)$alkylamino, di$(C_1-C_6)$alkylamino or halo;

$R_2$ is hydrogen or X;

$R_3$ is X or Y;

with the proviso that only one of the substituents $R_2$ and $R_3$ is X;

X is $C_2-C_6$ alkenyl; $C_2-C_6$ alkynyl; or phenyl; and

Y is selected from the group consisting of a saturated or unsaturated, optionally substituted, aliphatic hydrocarbon having 1 to 40 carbon atoms, wherein the hydrocarbon chain of the hydrocarbon is optionally interrupted by a heteroatom; an optionally substituted carbocyclic or heterocyclic, saturated, unsaturated or aromatic monocyclic or polycyclic group; and an aliphatic saturated or unsaturated hydrocarbon wherein the hydrocarbon is substituted with an optionally substituted carbocyclic or heterocyclic group and wherein the hydrocarbon chain of the hydrocarbon is optionally interrupted by a heteroatom.

4. Process according to claim 1, wherein in step a), the aldehyde of formula I is reacted with a compound of formula II wherein E and G are oxygen, in an aprotic solvent in the presence of an inorganic or organic acid catalyst at a temperature between 15 and 150° C.

5. Process according to claim 4, wherein the acid catalyst is selected from the group consisting of paratoluenesulphonic acid, hydrochloric acid, sulphuric acid and acetic acid.

6. Process according to any one of claims 4 or 5, wherein the acid catalyst is used in step a) in an amount of from 0.01 to 0.2 mol of catalyst per 1 mol of the aldehyde of formula I.

7. Process according to claim 1, wherein in step a) the aldehyde of formula I is reacted with a compound of formula II wherein E and G independently are a group —NR$_0$— where the group $R_0$ is as defined in claim 1, in an aprotic solvent at a temperature between 15 and 150° C.

8. Process according to any one of claims 1, 2, 4 and 5, wherein the reaction of the aldehyde of formula I with compound II is carried out in a solvent selected from the group consisting of toluene, acetonitrile, dimethylformamide and dimethylacetamide.

9. Process according to any one of claims 1, 2, 4 and 5, wherein in step b), the diastereoisomers are separated by chromatography or by crystallisation.

10. Process according to any one of claims 1, 2, 4 and 5, wherein in step c), the hydrolysis of the acid function is carried out by the action of 3 to 5 mol-% of a halohydric acid per 1 mol of the compound of formula III, in acetone as the solvent.

11. Process according to claim 10, wherein the halohydric acid is hydrochloric acid, which is added to the reaction medium in the form of silica impregnated with hydrochloric acid.

* * * * *